United States Patent [19]

Tatematsu et al.

[11] Patent Number: 4,987,031
[45] Date of Patent: Jan. 22, 1991

[54] CAPSULE

[76] Inventors: Shinzo Tatematsu, 145-25, Kitanishi-cho, Nara 639-11 Yamatokoriyama-shi; Kazuki Omata, 6-22-6, Meguro-honcho, Meguro-ku,, Tokyo 152; Tatsuo Hashimoto, 77-12, Koizumi, Ageo-shi, Saitama 362; Masato Takahashi, 4-116-18, Miyahara-cho, Ohmiya-shi, Saitama 330; Noriichi Ito, 2-3-28, Umamikita, Koryo-cho, Kitakatsuragi-gun Nara 635, all of Japan

[21] Appl. No.: 362,430

[22] PCT Filed: Oct. 3, 1988

[86] PCT No.: PCT/JP88/01011

§ 371 Date: Jun. 1, 1989

§ 102(e) Date: Jun. 1, 1989

[87] PCT Pub. No.: WO89/03206

PCT Pub. Date: Apr. 20, 1989

[30] Foreign Application Priority Data

Oct. 6, 1987 [JP] Japan ................ 62-253111

[51] Int. Cl.$^5$ ............. A61K 9/48; A61K 9/50; B01J 13/02
[52] U.S. Cl. ................ 428/402.2; 424/456; 424/491; 424/492; 428/402.24
[58] Field of Search ......... 428/402.2, 402.24; 424/456, 478, 492

[56] References Cited

U.S. PATENT DOCUMENTS

| | | | |
|---|---|---|---|
| 3,092,553 | 6/1963 | Fisher, Jr. et al. | 428/402.2 X |
| 3,436,452 | 4/1969 | Maierson | 428/402.2 X |
| 3,576,758 | 4/1971 | Emrick | 428/402.2 |
| 3,851,051 | 11/1974 | Miskel et al. | 424/455 |
| 4,609,403 | 9/1986 | Wittwer et al. | 424/456 X |

FOREIGN PATENT DOCUMENTS

| | | | |
|---|---|---|---|
| 51-15094 | 5/1976 | Japan . | |
| 51-101118 | 9/1976 | Japan . | |
| 58-62120 | 4/1983 | Japan . | |
| 0046215 | 3/1984 | Japan | 424/492 |

Primary Examiner—Richard D. Lovering

[57] ABSTRACT

The present invention relates to gelatin composite for the use of capsules to fill medicine and the like, coating agents or binding agents of tablets, casing materials and so on. A gelatin composite of the invention is characterized by comprising gelatin and polypeptide as an essential component, wherein the polypeptide is in the range of 15–70% by weight, referring to the total weight of the polypeptide and gelatin, and the gelatin has a gelly strength of 250 bloom or greater. The gelatin composite prevents insolubilization of the gelatin due to the passage of time without any degradation of shape-retaining ability of the gelatin composite.

1 Claim, No Drawings

CAPSULE

DESCRIPTION

1. Technical Field

This invention relates to gelatin composite for the use of capsules to fill medicine and the like, coating agents or binding agents of tablets, casing materials and so on.

2. Background Art

Some medicines, for example, are cased in capsules to prepare capsule medicines which are used with a purpose of easy taking or sure absorption at the digestive organ destined. A capsule for such use is required to have a shape-retaining ability which can retain the shape under various conditions, and to show disintegration which does not change with the passage of time.

The change of disintegration with the passage of time is said to be caused by that the gelatin, a main component of the capsule, reacts by themselves or with a substance enclosed in the capsule, and becomes insoluble as the time passes.

Japanese Patent Gazette (Kokai) No. 58-62120 discloses a soft capsule, which can prevent that kind of insolubilization of gelatin with the passage of time. The soft capsule is a gelatin composite comprising addition of polypeptide of 0.5-10% by weight of the gelatin. The soft capsule was devised to prevent the insolubilization by allowing the added polypeptide to react with an enclosed substance before gelatin reacts.

However, it was found by experiments of the present inventors that, in a case of that the substance enclosed is highly reactive, the amount of polypeptide consumption with the reaction seriously increase resulting in an unsufficient prevention of the insolubilization with the use of amount in the above range. Then, if polypeptide is added over the range to solve the unsufficient prevention, it turns out to lead to degradation of the shape-retaining ability of the gelatin composite or the products comprising it.

Considering these situations, the present invention was undertaken to provide gelatin composite which can prevent the insolubilization of gelatin due to the passage of time without any degradation of the shape-retaining ability of gelatin composite.

DISCLOSURE OF INVENTION

The invention provides a gelatin composite characterized by comprising gelatin and polypeptide as an essential component, wherein the polypeptide is in the range of 15-70% by weight, referring to the total weight of the polypeptide and gelatin, and the gelatin has a gelly strength of 250 bloom or greater.

Below is the detailed description of the invention.

Gelatin composite of this invention comprises gelatin and polypeptide as an essential component. Besides the two, the gelatin composite may be added with one or more of plasticizer, thickener, agent for coloring, etc. Some examples of the plasticizer are glycerin and sorbitol, and they may be employed solely or in combination. Some examples of thickener are gum arabic and alginic acid, and they may be employed solely or in combination. Some examples of agents for coloring are various food colors, and they may be employed solely or in combination.

Gelatin used in the invention is required to have a gelly strength of 250 bloom or greater. That is because, if the strength is below than 250 bloom, the shape-retaining ability of gelatin composite or products comprising it degrades even though the amount of the added polypeptide is relatively small. Herein the gelly strength was tested in accordance with JIS K 6503 (1977 edition).

Gelatin may be produced under mild conditions preventing any degradation factor of its gelly strength in order to keep a high gelly strength. However, it may be prepared in other methods, or obtained from the market where gelatins having a gelly strength of 250 bloom or greater are available.

The kind of polypeptide for the invention is not specialized. However, the polypeptide ratio should be here in the range of 15-70% by weight, referring to the total weight of the polypeptide and gelatin. If polypeptide is added over the range, gelatin composite or products comprising it may have a very low shape-retaining ability and will be unfavorable for practical use. If polypeptide is added under the range, the prevention effect on the insolubilization of gelatin with the passage of time becomes unsufficient. This is also practically unfavorable.

Polypeptide to be employed in the invention is preferred to have a molecular weight of about 5000-10,000. Because under a molecular weight of 5000 the polypeptide may result in an undesiably low shape-retaining ability, and over a molecular weight of 10,000, it may not prevent effectively the insolubilization of gelatin with the passage of time.

The insolubilization of gelatin with the passage of time is prevented efficiently because gelatin composite of this invention comprises polypeptide. More specifically, that is because, when the gelatin composite or products comprising it gets in touch with the reacting substance enclosed, the polypeptide chemically reacts with the substance before the gelatin does. Herein, the ratio of the polypeptide is in the above-specified range so that, even if the touching substance is of a high reactivity, the lowering in solubility of the gelatin is prevented over a period of time, and the shape-retaining ability of products comprising the gelatin composite does not decrease significantly. Besides, although the polypeptide is mixed in a large amount as described above, the shape-retaining ability is maintained almost on the same level as that of the products prepared by the existing gelatin composite for capsules, because the subject gelatin has a gelly strength of 250 bloom or greater.

Since gelatin composite of this invention is such as shown above, the degree of insolubilization of gelatin in it with the passage of time becomes small without any degradation of shape-retaining ability, and furthermore, the degree of insolubilization with the passage of time is small enough even when the gelatin composite come in contact with a substance of high reactivity.

BEST MODE FOR CARRYING OUT THE INVENTION

Some examples of this invention will be explained in comparison with referring examples which deviate from a range of numerical values of this invention. However, this invention is not limited to these examples. Polypeptides used in the following examples have molecular weights of about 8000.

EXAMPLES 1-5

According to the procedure shown in Table 1, sheets comprising the subject gelatin composite were obtained by dissolving each group of materials under warm conditions, mixing it well, cooling it down after forming it into a sheet, and then drying it at a low temperature.

REFERENCE EXAMPLES 1–4

Dissolving under warm conditions followed by mixing was carried out according to the procedure shown in Table 1. Then, sheets comprising the common gelatin composite were obtained in the same method as the above examples.

As to each of the examples 1–5 and reference examples 1–4, gelly strength was tested on the gelatin and on the mixture of gelatin and polypeptide, and disintegration was tested on each sheet obtained. Results are shown in Table 1.

Gelly strength test was conducted in accordance with JIS K 6503 (1977 edition).

Disintegration of sheets was tested on each of sheets obtained immediately after preparation, after a storage for six months at 40° C., and after dipping in a liver oil for one month at 20° C. The tests results were performed by determining time necessary for dissolution at 37° C. with a disintegration apparatus. Results are shown in Table 1 by time for dissolving 0.2 g of sheets.

prises gelatin and polypeptide in the above-specified ratio and other components where necessary.

Some examples of gelatin composite on a raw material stage of this invention are a powder prepared by mixing gelatin and polypeptide in the above-specified ratio, a powder prepared by mixing this powder with other materials where necessary, or a solution comprising such powders.

Examples of gelatin composite on a product stage of this invention are capsules or microcapsules to enclose medicines or the like, casing materials in the form of sheet or film, or binding agents or coating agents for tablets, etc.

In this invention, some examples of gelatin composite on a stage between the raw material and product stages are sheets to form capsules, and sheets or films to form casing materials in a bag form or the like.

In the case that gelatin composite of the invention is led to capsules, capsules may be either a soft or a hard type, or a medium type between those. They may take a form of microcapsule. Shape or scale is not limited.

Though the capsules comprising gelatin composite in the invention are different from prior capsules in a high gelly strength of gelatin and in a large ratio of polypeptide, they may be prepared by the existing methods and

TABLE 1

| Composition of Aqueous Solution of Gelatin Composite and Physical Properties of Sheets | Example 1 | Reference Example 1 | Example 2 | Reference Example 2 | Example 3 | Reference Example 3 | Reference Example 4 | Example 4 | Example 5 |
| --- | --- | --- | --- | --- | --- | --- | --- | --- | --- |
| Components (g) | | | | | | | | | |
| Gelatin | 70 | 70 | 80 | 90 | 35 | 25 | 92 | 50 | 50 |
| Polypeptide | 30 | 30 | 20 | 10 | 65 | 75 | 8 | 50 | 50 |
| Glycerin | 40 | 40 | 40 | 40 | 40 | 40 | 40 | 40 | 40 |
| Water | 260 | 260 | 260 | 260 | 260 | 260 | 260 | 260 | 260 |
| Gelly Strength of Gelatin (bloom) | 260 | 150 | 260 | 260 | 350 | 260 | 150 | 260 | 350 |
| Gelly Strength of Mixture of Gelatin and Polypeptide (bloom) | 150 | 40 | 180 | 210 | 100 | 25 | 100 | 100 | 100 |
| Disintegration of Sheets (min.) | | | | | | | | | |
| Immediately After Preparation | 5 | 5 | 5 | 10 | 5 | 5 | 10 | 5 | 5 |
| After storage for Six Months | 10 | * | 10 | 24 | 5 | * | 24 | 5 | 5 |
| After Dipping in Liver Oil for One Month at 20° C. | 18 | * | 29 | 45 | 16 | * | Insolubilized | 16 | 16 |

*Sheets were too soft to test, indicating no shape-retaining ability.

As shown in Table 1, among reference examples 1–4 deviating from the range of numerical values specified in the subject invention, reference examples 1 and 3 have no shape-retaining ability and reference example 2 shows a large decrease in disintegration with the passage of time. Reference example 4 showed still large disintegration and was insolubilized with dipping in a liver oil. In contrast, all the examples 1–5 show smaller values in disintegration with the passage of time than the reference examples 2 and 4 and also, were superior in disintegration on testing immediately after preparation, after a storage for six months following after the preparation, and after dipping in a liver oil for one month.

INDUSTRIAL APPLICABILITY

Gelatin composite of the invention may be applicable to gelatin composite on a raw material stage, on a product stage and a medium stage between those, if it comequipments so far used in this field. Consequently, there is no need to make any new plant and equipment investment.

When capsules are prepared from the subject gelatin composite, the working conditions for so far known capsules can be applied without meaningful modification. For example, aqueous solution comprising the subject gelatin and polypeptide in the above-specified ratio and, if necessary, other materials is prepared. The solution is dried to form sheet according to a usual method. Out of the sheet, capsules may be obtained with such a continuous method as filling of contents with a rotary filling machine, or with Plate Method using the said sheet. Instead of preparing sheet in advance, capsules may be prepared by such a method as Globex method wherein contents is filled together with production of capsules. Method of preparing capsules comprising the subject gelatin composition does not have a special limitation.

Substances enclosed in capsules or microcapsules comprising the gelatin composition are of various kinds and no limitation; for example, medicines, foods, etc. The enclosed substances are not limited to liquid materials.

Microcapsules employing the subject gelatin composite as a wall material may be obtained, for example, by preparing aqueous solution comprising the subject gelatin composite, adding in it one or more oily or solid core materials, then mixing it, and the mixture being subjected to a spray drying.

Casing material comprising the subject gelatin composite may be obtained, for example, by preparing sheet consisting of the gelatin composite and making it into the form of bag or the like. Such a casing material may be used as an envelope of solid or oily mateials.

Coated film being composed of the subject gelatin composite, may be obtained with a liquid for smoothing, a liquid for coloring, and the like, which are prepared, for example, by adding gelatin of the specified gelly strength and polypeptide in the specified ratio together or separately, instead of the common gelatin material so far employed. The coated film may be obtained by coating such a solution on the surface of tablets. Some examples of coatings are sugar coating, water soluble coating and enteric-soluble film-coating.

In making use of the subject gelatin composite as a binding agent for tablets, a binding agent, for example, for condensed tablets may be prepared by adding gelatin of the specified gelly strength and polypeptide in the specified ratio together or separately instead of the common gelatin, which is a binding agent in production of condensed tablets.

We claim:

1. A capsule the wall material of which consists essentially of 85–30% by weight of gelatin having a gelly strength of 250 bloom or greater, and 15–70% by weight of a polypeptide having a molecular weight of about 5,000–10,000.

* * * * *

UNITED STATES PATENT AND TRADEMARK OFFICE
CERTIFICATE OF CORRECTION

PATENT NO. : 4,987,031
DATED : January 22, 1991
INVENTOR(S) : TATEMATSU et al

It is certified that error appears in the above-identified patent and that said Letters Patent is hereby corrected as shown below:

On the title page, insert after Item [76],

--[73]  Assignee: NITTA GELATIN INC., Osaka, Japan; and TAISHO PHARMACEUTICAL CO., LTD., Tokyo, Japan--.

Signed and Sealed this

Eleventh Day of August, 1992

*Attest:*

DOUGLAS B. COMER

*Attesting Officer*      *Acting Commissioner of Patents and Trademarks*